(12) United States Patent
Mehus et al.

(10) Patent No.: US 7,974,920 B2
(45) Date of Patent: Jul. 5, 2011

(54) BENEFIT PLANNING

(75) Inventors: William P. Mehus, Plymouth, MN (US); Jimmy R. Willard, Circle Pines, MN (US); Paul A. Walther, Hopkins, MN (US)

(73) Assignee: Outsource One, Inc., Minneapolis, MN (US)

( * ) Notice: Subject to any disclaimer, the term of this patent is extended or adjusted under 35 U.S.C. 154(b) by 1159 days.

(21) Appl. No.: 11/395,361

(22) Filed: Mar. 31, 2006

(65) Prior Publication Data

US 2007/0233515 A1 Oct. 4, 2007

(51) Int. Cl.
*G06Q 40/00* (2006.01)

(52) U.S. Cl. .................. 705/41; 705/2; 705/14; 705/38; 235/375; 707/783

(58) Field of Classification Search ........ 726/4; 725/46; 705/3; 463/1
See application file for complete search history.

(56) References Cited

U.S. PATENT DOCUMENTS

| | | | |
|---|---|---|---|
| 5,655,085 A | 8/1997 | Ryan et al. | |
| 5,724,379 A | 3/1998 | Perkins et al. | |
| 6,735,569 B1 | 5/2004 | Wizig | |
| 6,826,541 B1 | 11/2004 | Johnston et al. | |
| 7,305,347 B1 * | 12/2007 | Joao | 705/1 |
| 7,424,449 B2 * | 9/2008 | Goel | 705/26.7 |
| 2002/0022982 A1 * | 2/2002 | Cooperstone et al. | 705/7 |
| 2002/0049617 A1 | 4/2002 | Lencki et al. | |
| 2002/0087444 A1 * | 7/2002 | DiPiero et al. | 705/35 |
| 2002/0095316 A1 * | 7/2002 | Toan et al. | 705/4 |
| 2002/0128879 A1 | 9/2002 | Spears | |
| 2002/0147617 A1 * | 10/2002 | Schoenbaum et al. | 705/4 |
| 2002/0169727 A1 * | 11/2002 | Melnick et al. | 705/400 |
| 2003/0065534 A1 | 4/2003 | McCartney | |
| 2003/0120511 A1 | 6/2003 | Legnini | |
| 2003/0149596 A1 | 8/2003 | Bost | |
| 2003/0229522 A1 * | 12/2003 | Thompson et al. | 705/4 |
| 2004/0049397 A1 * | 3/2004 | Leisure et al. | 705/1 |
| 2004/0059626 A1 | 3/2004 | Smallwood | |
| 2004/0103002 A1 | 5/2004 | Colley et al. | |
| 2004/0128172 A1 | 7/2004 | Van Cleave et al. | |
| 2004/0249719 A1 | 12/2004 | Urpani | |
| 2005/0149359 A1 | 7/2005 | Steinberg et al. | |
| 2005/0182659 A1 | 8/2005 | Huttin | |
| 2005/0182660 A1 | 8/2005 | Henley | |
| 2005/0240613 A1 * | 10/2005 | Logan, Jr. | 707/102 |
| 2005/0286709 A1 | 12/2005 | Horton et al. | |
| 2007/0244767 A1 * | 10/2007 | Goel | 705/26 |

OTHER PUBLICATIONS

How to make best choices for survivor benefits using a computer program, Dec. 6, 2004 (Hebeler).*
Decision support helps workers pick plans, Employee Benefit News, Jill Elswick, Nov. 1, 2001(Elswick).*
Subimo, "Health Care Cost Calculator", http://www1.subimo.com/ca/app/bcbsmngrp/CoverageAdvisor, Mar. 30, 2006, (pp. 1-8).

* cited by examiner

*Primary Examiner* — James P Trammell
*Assistant Examiner* — Chika Ojiaku
(74) *Attorney, Agent, or Firm* — Brooks, Cameron Huebsch, PLLC

(57) ABSTRACT

Methods, computer readable media, and systems including program instructions are provided for use with benefit planning. A method embodiment includes providing terms for a number of benefit plans available to a potential participant. The embodiment also includes receiving an estimate of benefits to be used by the potential participant. The embodiment further includes displaying together an estimate of expenses to be incurred by the potential participant under each of the benefit plans based on the terms and the estimate of benefits to be used.

22 Claims, 7 Drawing Sheets

Fig. 3

Medical Coverage

| View All | Statement | Benefit Info | Help | Finish | Exit |

Back

Elect New Plan:
Who will you enroll in the Medical Plan you choose?

○ Waive Benefit ←—410
○ Single Coverage ←—420
⦿ Family Coverage: (Below are the dependents loaded in the system.) ←—430
  ☑ Matthew Public ⎫
  ☑ Sally Public      ⎬ 435
  ☑ Jane Public     ⎭

Options

Continue to Elect New Plan
You must complete the form (left) to elect a new plan

*Fig. 4*

Medical Expense Estimator Worksheet

The following questions are intended to help you estimate what your total annual Out-of-Pocket Expenses will be for your Medical Plan this year. This tool uses your actual Copay amounts and your Coinsurance percentage along with some assumptions about the average price of each of the medical services listed.

Enter the estimated number of times you (and all family members to be covered under the medical plan) will be receiving each kind of service.

Visit/Yr

Medical Primary Care Physician Visit [1]

Specialist Visit [2]

Routine Wellness Exam/Visit [2]

Urgent Care Visit [1]

Emergency Room Visit [2]

— 510

Estimate the number of prescription purchases you (and all family members to be covered under the medical plan) will receive over the course of the year. *Example: 3 prescriptions you have filled monthly would be 12 occurrences.*

RX/Yr (30 Days)

Generic [12]

Brand [0]

Non-Preferred [0]

— 523

RX/Yr (30 Days)

[0] [0] [0] — 527

How many Outpatient Surgery visits do you and any covered dependents anticipate this year? [0] — 530

How many Inpatient Surgery Visits or Hospital Stays, including maternity stays, do you and any covered dependents anticipate this year? [0] — 540

If you listed more than one Inpatient Visit above, how many different people on your plan will experience an Inpatient Visit? [0] — 550

*Fig. 5*

Life Worksheet

Life Insurance Needs Table
(Multiple X annual income)

| Age | Generally Recommended |
|---|---|
| 20 - 30 | 15 X |
| 31 - 40 | 15 X |
| 41 - 50 | 10 X |
| 51 - 60 | 7 X |
| 61 - 70 | 5 X |
| 66 or older | 3 X |

Non-working Spouse Coverage: Insurance companies use $35,000 as the income value for a non-working spouse. Use $35,000 for income and the multiple for your age group when calculating the coverage amount. Insurance coverage on a non-working spouse cannot normally exceed 90% of the coverage on the working spouse.

Your Information:
- Multiple X (from above table): 10 X — 721
- Your current annual income: 36000 — 722
- How much current life coverage do you have?
- Basic Employer Sponsored Life Insurance: 50000 — 723
- Employer Sponsored Supplemental Life Insurance: 50000 — 724
- Employee Paid Marketplace Life: 0 — 725
- Other Life Insurance Coverage: 100000 — 726
- Recommended Coverage: 360000 — 727
- Current Coverage: 200000 — 728
- Difference: $160,000 — 729

Spouse Information:
- Multiple X (from above table): 7 X
- Spouse current annual income: 60000
- How much current life coverage does your spouse have?
- Basic Employer Sponsored Life Insurance: 100000
- Employer Sponsored Supplemental Life Insurance: 50000
- Employee Paid Marketplace Life: 0
- Other Life Insurance Coverage: 30000
- Recommended Coverage: 420000
- Current Coverage: 180000
- Difference: $240,000

*Fig. 7*

BENEFIT PLANNING

BACKGROUND

In the field of benefit planning, an individual can enroll in various benefit plans. As examples, an individual can enroll in a medical benefit plan, a dental benefit plan, a vision benefit plan, a life insurance benefit plan, a disability benefit plan, and other types of benefit plans. An individual who is enrolled in a benefit plan is considered to be a participant or a member in that plan. A participant in a benefit plan can receive certain benefits from a provider or a carrier of the benefit plan ("plan provider"), as defined under the terms of the benefit plan.

Various expenses can be incurred by a participant under the terms of a benefit plan. A plan provider can charge a certain premium for a participant to participate in a particular benefit plan. Additionally, a plan provider can charge certain deductibles, copays, and coinsurance percentages for a participant to use various products and/or services covered by a particular benefit plan.

The expenses incurred by a participant under a particular benefit plan can be paid in different ways. The participant and/or a sponsor of the benefit plan, such as the participant's employer, can directly pay for some or all of these expenses. In some instances, the participant and/or the sponsor can contribute funds to a benefits account for the participant. Funds from the benefits account can then be used to pay for some or all of the expenses incurred by the participant.

Before enrolling in a benefit plan, it can be useful for a potential participant to estimate expenses to be incurred by their participation in benefit plans and by their use of benefits under the benefit plans. However, it can be difficult for a potential participant to estimate these expenses. In order to estimate expenses to be incurred under benefit plans, a potential participant would use information from a variety of sources, which may not be readily available to the potential participant. Further, it can also be difficult for a potential participant to compare expenses under one benefit plan with expenses under another benefit plan, since the terms of the benefit plans may be quite different. As a result, it can be difficult for an individual to estimate and compare expenses to be incurred by their participation in various benefit plans.

BRIEF DESCRIPTION OF THE DRAWINGS

FIG. 3 is a viewable interface illustrating an embodiment for receiving personal information according to the present disclosure.

FIG. 4 is a viewable interface illustrating an embodiment for selecting benefit coverage according to the present disclosure.

FIG. 5 is a viewable interface illustrating an embodiment for estimating benefits to be used according to the present disclosure.

FIG. 7 is a viewable interface illustrating an embodiment for displaying a recommended level of benefits according to the present disclosure.

DETAILED DESCRIPTION

Embodiments of the present disclosure include methods, computer readable media, and systems including program instructions for use in benefits planning. A method embodiment includes providing terms for a number of benefit plans available to a potential participant. The embodiment also includes receiving an estimate of benefits to be used by the potential participant. The embodiment further includes displaying together an estimate of expenses to be incurred by the potential participant under each of the benefit plans based on the terms and the estimate of benefits to be used.

An individual can use various embodiments of the present disclosure to estimate expenses to be incurred by their participation in various benefit plans and by their use of benefits under the benefit plans. In some embodiments of the present disclosure, a potential participant can also compare estimates of expenses to be incurred under a number of benefit plans offered by one or more plan providers. A potential participant can use such a comparison to select a particular benefit plan into which they can enroll.

Embodiments of the present disclosure can be performed by software, firmware, hardware, application modules, and the like. These embodiments can use program instructions resident on and/or executable by one or more ASICs, devices (e.g. memory devices, computing devices, network devices, etc.), systems, or networks shown herein or otherwise. The embodiments of the present disclosure are not limited to any particular operating environment or to instructions written in any particular programming language. Software, firmware, and/or processing modules, suitable for carrying out embodiments of the present disclosure, can be resident on one or more devices in one or more locations.

In some embodiments of the present disclosure, a system can include a processor, a memory connected to the processor, and program instructions storable in the memory and executable by the processor. In other embodiments, program instructions, including instructions for causing a device to perform a method, can be stored on various forms of computer readable media, such as RAM, ROM, hard disks, floppy disks, CDs, DVDs, flash drives, flash memory, etc.

Figure 1:
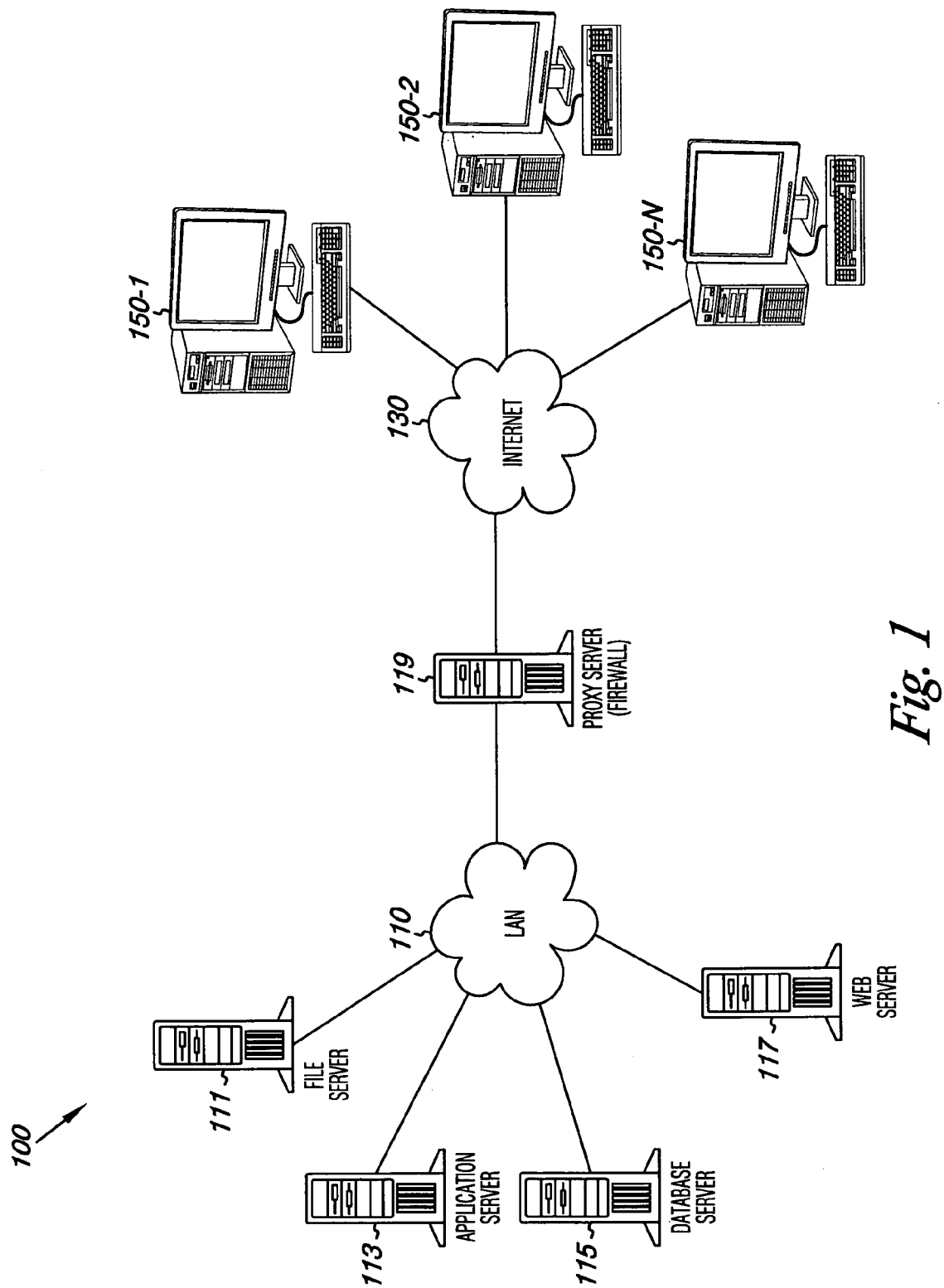
FIG. 1 illustrates an exemplary computing network suitable for implementing embodiments of the present disclosure.

FIG. 1 illustrates an exemplary computing network 100 suitable for implementing embodiments of the present disclosure. The network 100 includes a file server 111, an application server 113, a database server 115, a web server 117, and a proxy server 119, networked together via a local area network (LAN) 110. The network 100 also includes computing device 150-1, computing device 150-2, and computing device 150-N (where "N" represents a scalable number), each connected to the Internet 130. The LAN 110 is also connected to the Internet 130 through the proxy server 119.

A number of network devices, e.g. computing devices, servers, computing peripherals, etc., can be networked together via the LAN 110. Network devices can also be networked together via other kinds of networks, such as wide area networks (WANs), wireless networks, etc. The servers networked together via the LAN 110 can perform various functions. The file server 111 can store various files and can provide access to those files through the LAN 110. The application server 113 can store program applications with various program instructions (e.g., computer executable instructions) which can be executable over the LAN 110. The database server 115 can store various databases and can provide access to those databases through the LAN 110. For example, the database server 115 can store a database with information about a number of benefit plans and estimates of expenses for benefits, as described in connection with FIG. 2. The web server 117 can provide various services associated with the Internet, including access to the World Wide Web. For example, the web server 117 can store one or more web pages associated with a website for benefit planning, e.g., as described in connection with embodiments of FIGS. 2-8. The proxy server 119 can connect the LAN 110 to the Internet 130 and can serve as a firewall between them.

A number of computing devices can connect to the Internet 130, and/or one or more other networks. Computing devices can connect to the Internet 130 in various ways, such as through dial-up connections, DSL lines, cable lines, T-1 lines, networks, and other connections. Through the Internet, computing devices can transmit and/or receive various information, such as information contained in one or more web pages associated with a website. According to various embodiments of the present disclosure, an individual can use a computing device to access a website for benefit planning as described in connection with embodiments of FIGS. 2-8.

Figure 2:
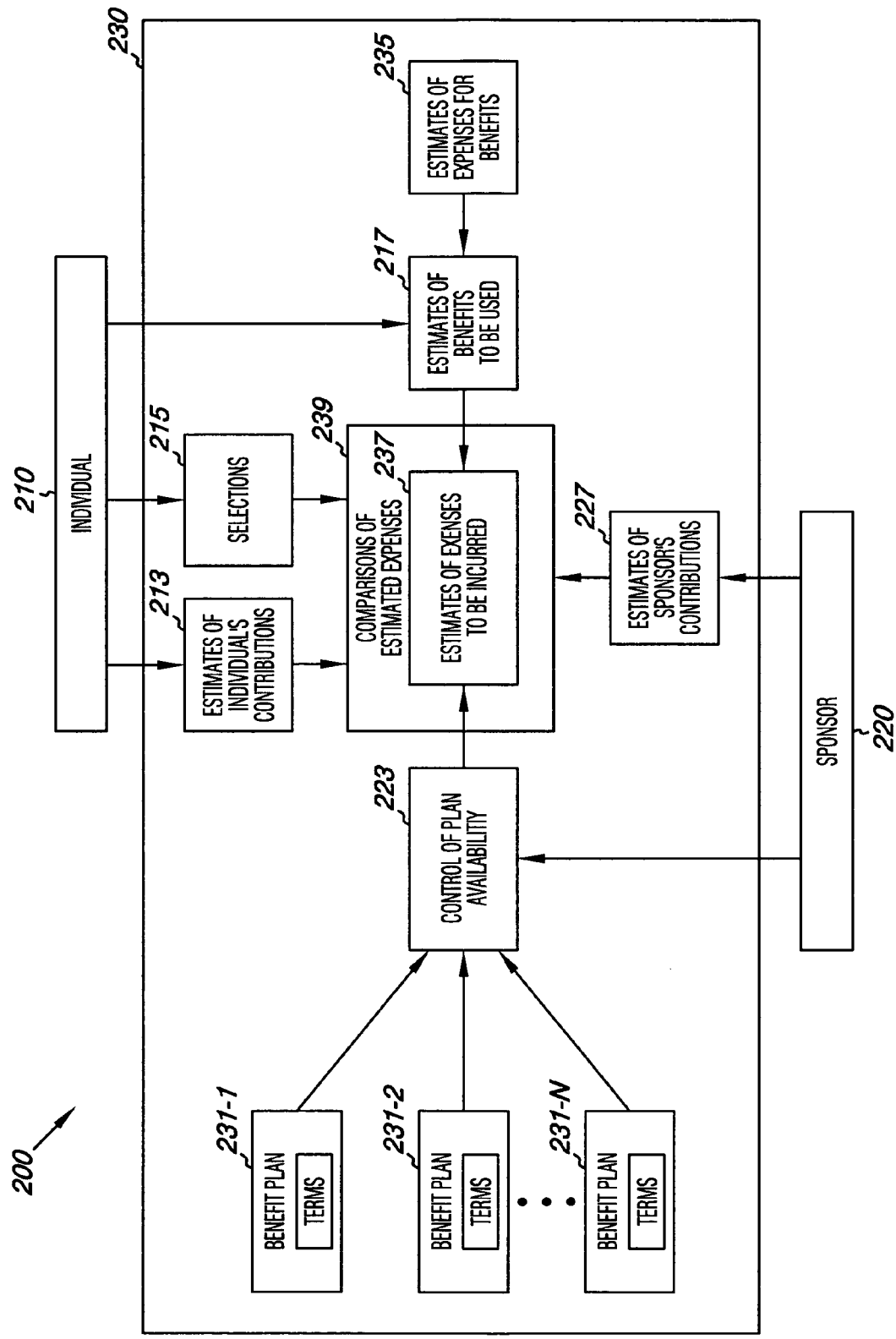
FIG. 2 illustrates a block diagram for an embodiment of benefit planning according to the present disclosure.

FIG. 2 illustrates a block diagram 200 for an embodiment of benefit planning according to the present disclosure. The diagram 200 illustrates an individual 210 and a sponsor 220 interacting with program instructions 230. The program instructions 230 includes various program instructions, which can execute to perform various functions as described below. The program instructions 230 can execute to receive estimates of the individual's contributions 213, receive selections 215 from the individual 210, receive an estimate of benefits to be used 217, receive information associated with a control of plan availability 223, and receive an estimate of the sponsor's contributions 227. The program instructions 230 can also execute to store and/or access information including information about a first benefit plan 231-1, information about a second benefit plan 231-2, information about an Nth benefit plan 231-N (where "N" represents a scalable number), and information about estimates of expenses for benefits 235. Further, the program instructions 230 can execute to perform comparisons 239 of calculated estimates of expenses to be incurred 237.

The individual 210 can be a potential participant in a benefit plan. The sponsor 220 can be an entity which can offer one or more benefit plans to the individual 210. As examples, the sponsor 220 can be an employer of the individual 210, an educational institution which the individual 210 attends, an organization with which the individual 210 does business, or a benefit plan administrator. In various embodiments, the embodiment of FIG. 2 may include interaction from more than one sponsor or the method may include interaction from no sponsor. The program instructions 230 can execute, in various embodiments, to perform various functions via a website with one or more associated web pages.

The program instructions 230 can execute to receive particular log-in information for the individual 210. The program instructions 230 can execute to use this particular log-in information to determine an identity of the individual 210 associated with the particular log-in information. The program instructions 230 can also execute to use this particular log-in information to determine one or more benefit plans associated with the particular log-in information and available to the individual 210. Further, the program instructions 230 can execute to use this particular log-in information to provide access to the individual 210 to provide the estimates of the individual's contributions 213, to provide the selections 215, to provide the estimates of benefits to be used 217, and to receive comparisons 239 of calculated estimates of expenses to be incurred 237, as described below.

The program instructions 230 can also execute to receive particular log-in information for the sponsor 220. The program instructions 230 can execute to use this particular log-in information to determine an identity of the sponsor 220 associated with the particular log-in information. The program instructions 230 can also execute to use this particular log-in information to determine one or more benefit plans associated with the particular log-in information and offered by the sponsor 220. Further, the program instructions 230 can execute to use this particular log-in information to provide access to the sponsor 220 to control the availability of benefit plans 223 and to provide estimates of the sponsor's contributions 227, as described below.

The program instructions 230 can execute to store and/or access various information about one or more benefit plans. The program instructions 230 can execute to store and/or access information about the first benefit plan 231-1, information about the second benefit plan 231-2, and information about the Nth benefit plan 231-N. These benefit plans can be medical benefit plans, dental benefit plans, vision benefit plans, life insurance benefit plans, disability benefit plans, and/or other types of benefit plans.

For each of the benefit plans 231-1 through 231-N, the information about the benefit plan can include the terms of the benefit plan, which can define certain benefits that a plan participant can receive from a plan provider, as well as certain expenses that a plan participant can incur under the benefit plan. Such terms can include a certain premium for an individual to participate in the benefit plan, as well as one or more of certain deductibles, copays, and coinsurance percentages for a participant to use various products and/or services covered by the benefit plan. In various embodiments of the present disclosure, the information about a benefit plan can be an electronic version of a summary plan document (SPD) stored in a database server, such as the database server 115 of FIG. 1.

In various embodiments of the present disclosure, the sponsor 220 can control the availability 223 of the benefit plans 231-1 through 231-N to the individual 210. The program instructions 230 can execute to receive a selection from the sponsor 220 and can further execute to use that selection to determine which benefit plan(s) from the benefit plans 231-1 through 231-N are available to the individual 210 for enrollment. The program instructions 230 can also execute to receive from the individual 210 the selection 215 for enrolling the individual 210 into a particular benefit plan from among the available benefit plan(s), as described in connection with the embodiment of FIG. 6.

The program instructions 230 can execute to store and/or access information about the estimates of expenses for benefits 235. The estimates of expenses for benefits 235 can include estimates for expenses of various products and/or services covered under a particular benefit plan. As examples, an estimate of an expense for a benefit can be $50 for a prescription medication or $250 for a medical examination by a physician. In various embodiments, these estimates can be actual expenses, provided by sellers of products and providers of services, and/or statistically calculated estimates based on data for a number of products and/or services from a number of sellers and/or providers. In various embodiments of the present disclosure, the estimates of expenses for benefits 235 can be stored in a database server, such as the database server 115 of FIG. 1.

The program instructions 230 can execute to receive estimates of benefits to be used. The program instructions 230 can execute to receive from the individual 210 one or more estimates of benefits to be used 217 by the individual 210 and/or to be used by others covered under a benefit plan for the individual 210. In various embodiments, these estimates of benefits to be used 217 can include estimates for particular types and frequency of benefits to be used. For example, these estimates can include estimates for particular health care benefits such as health products and/or health services to be used, as described in connection with the embodiment of FIG. 5. The estimates of benefits 217 can, in some embodiments, be estimates for a particular period of time. As an example, the individual 210 can provide estimates of benefits to be used 217 over a period of one year or for some other length of time. The individual 210 can provide the estimates of benefits to be used 217 based on criteria of their own choosing, such as an assessment of benefits previously used and/or currently used, and/or by a forecast of future needs for benefits.

The program instructions 230 can execute to receive estimates of contributions to be made to offset expenses to be incurred by the individual 210 and/or by others to be covered with the individual 210 under various benefit plans. The program instructions 230 can execute to receive from the individual 210 the estimates of the individual's contributions 213, e.g., pre-tax contributions from an existing health savings account (HSA), a flexible savings account (FSA), a health reimbursement account (HRA), etc. The program instructions can also execute to receive from the sponsor 220 the estimates of the sponsor's contributions 227. The estimates of the individual's contributions 213 and the estimates of the sponsor's contribution 227 can be various amounts, including zero.

In various embodiments, some or all of the contributions from the individual 210 and/or the sponsor 220 can be used to pay for some or all of the expenses to be incurred 237 under a benefit plan. Some or all of these contributions can, in various embodiments, be made to a benefits account for the individual 210. For example, the benefits account can be a health benefits account such as a HSA, a FSA, a HRA, or another kind of health benefits account. In various embodiments, one or more such benefits accounts may be used, or no benefits accounts may be used. Funds from the benefits account can be used to pay for some or all of the expenses to be incurred 237 by the individual 210 and/or by others to be covered with the individual 210 under various benefit plans 231-1, . . . , 231-N.

The program instructions 230 can execute to calculate the estimates of expenses to be incurred 237 by the individual 210 and/or by others to be covered with the individual 210 under each of the benefit plans 231-1 through 231-N that are available to the individual 210 through the control of the plan availabilities 223. The program instructions 230 can execute to calculate the estimates of expenses to be incurred 237 based on the estimates of benefits to be used 217 and the estimates of expenses for benefits 235 under the terms of the available benefit plans.

As an example, the estimated expense 235 for a medical examination by a physician may be $250, the estimate of benefits to be used 217 may include an estimate of two such medical examinations to be used in a year, and a particular benefit plan available to the individual 210 may provide terms under which a plan participant can receive the benefit of such a medical examination for a copay of $25 and payment of a 20% coinsurance percentage after a $100 deductible is paid. In this example, the program instructions 230 can execute to calculate the estimate of expenses to be incurred 237 including $500 for the two examinations, with the individual 210 as a potential participant to pay estimated expenses of $100 for the deductible, $80 for the coinsurance percentage on the remaining $400, and $50 for the two copays. The program instructions 230 can also execute to add the $100, the $80, and the $50 to obtain a $230 estimate of out-of-pocket expenses as part of the estimate of expenses to be incurred 237 for the individual 210 to use these benefits under the particular benefit plan.

The program instructions 230 can also execute to calculate the estimates of expenses to be incurred 237 to include one or more offsets from estimates of various contributions, as described above. The program instructions 230 can execute to perform these calculations based on the estimates of the individual's contributions 213, and the estimates of the sponsor's contributions 227, under the terms of the available benefit plans, which can include terms for using finds from various benefits accounts.

The program instructions 230 can display the estimates of expenses to be incurred 237 as the comparisons of estimated expenses 239 under various benefit plans. The program instructions 230 can execute to display the comparisons of estimated expenses 239 including the estimates of expenses to be incurred 237 by the individual 210 and/or by others to be covered with the individual 210 under each of the benefit plans 231-1 through 231-N that are available to the individual 210 through the control of the plan availability 223 by the sponsor 220. The program instructions 230 can execute to calculate the estimated expenses to be incurred 237 based on the estimates of benefits to be used 217 and the estimates of expenses for benefits 235 as offset by the estimates of the individual's contributions 213, and the estimates of the sponsor's contributions 227, all under the terms of the available benefit plans. In various embodiments, the comparisons of estimated expenses 239 can include estimates for a number of available benefit plans, displayed together, as described in connection with the embodiment of FIG. 6.

FIGS. 3-7 illustrate various viewable interfaces for benefit planning according to embodiments of the present disclosure. Program instructions, such as the program instructions 230 in the embodiment of FIG. 2, can execute to display such viewable interfaces, receive various inputs from a user, and perform various functions as described in detail below. In various embodiments, the viewable interfaces of FIGS. 3-7 can be one or more web pages, which are accessible via the Internet, e.g., as a website. However embodiments of the present disclosure are not limited to this form of viewable interface. Program instructions can also execute, in various embodiments, to provide such viewable interfaces for benefit planning as screens displayed on a stand-alone computing device or other electronic device.

FIGS. 3-7 include example information for an individual who is a potential participant in a benefit plan. This example information is included for illustrative purposes and is not intended to limit the scope of the present disclosure. The example information in the embodiments of FIGS. 3-7, may vary from figure to figure, unless otherwise stated.

Figure 6:
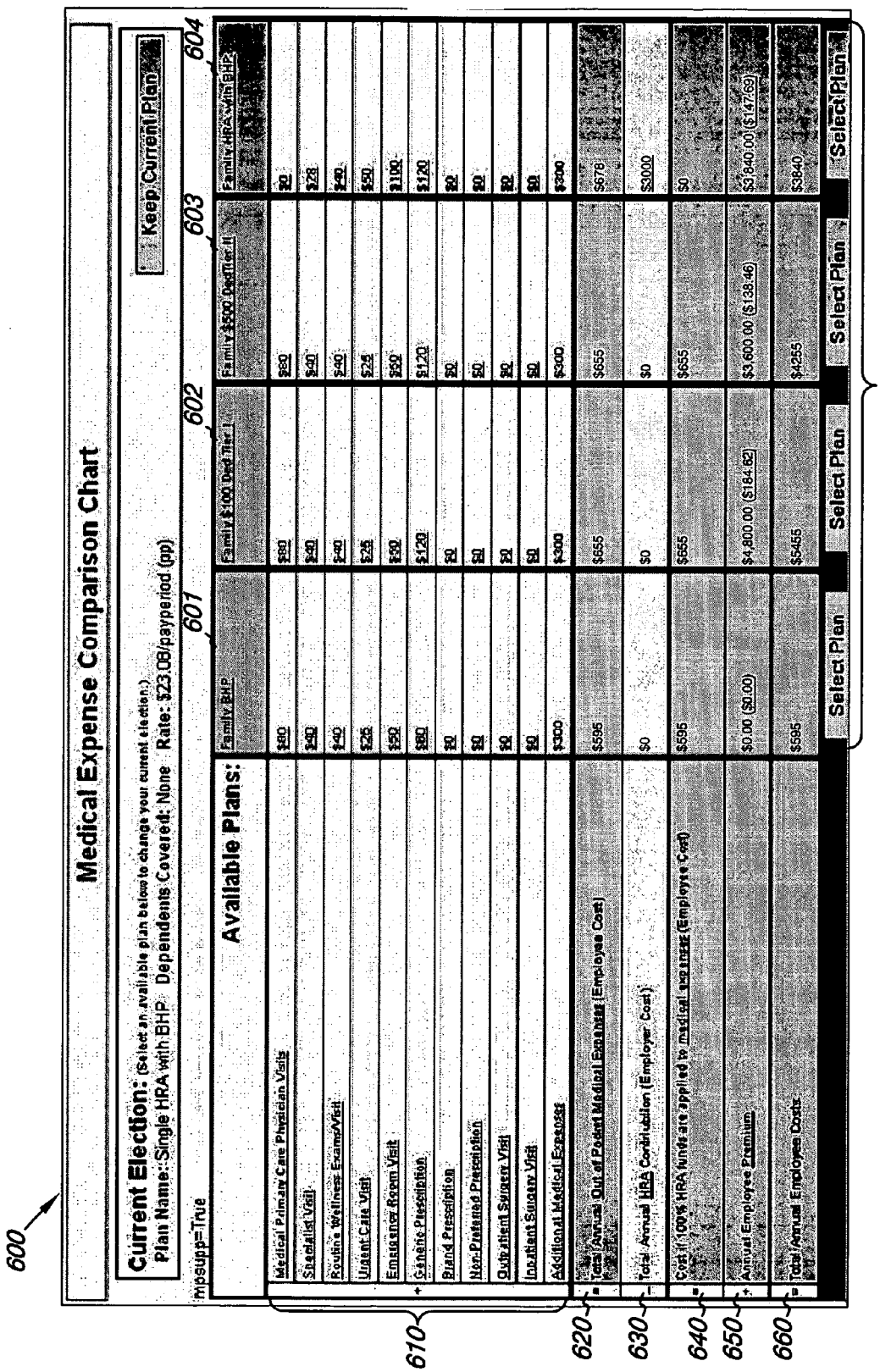
FIG. 6 is a viewable interface illustrating an embodiment for displaying estimates of expenses under benefit plans according to the present disclosure.

FIGS. 4-6 illustrate embodiments of the present disclosure for use with medical benefit plans. FIG. 7 illustrates embodiments of the present disclosure for use with life insurance benefit plans. These benefit plans are included for illustrative purposes and are not intended to limit the scope of the present disclosure to any particular benefit, benefit product, or type of benefit plan. Embodiments of the present disclosure can be used with various types of benefit plans, such as medical benefit plans, dental benefit plans, vision benefit plans, life insurance benefit plans, disability benefit plans, and other types of benefit plans.

Figure 3:
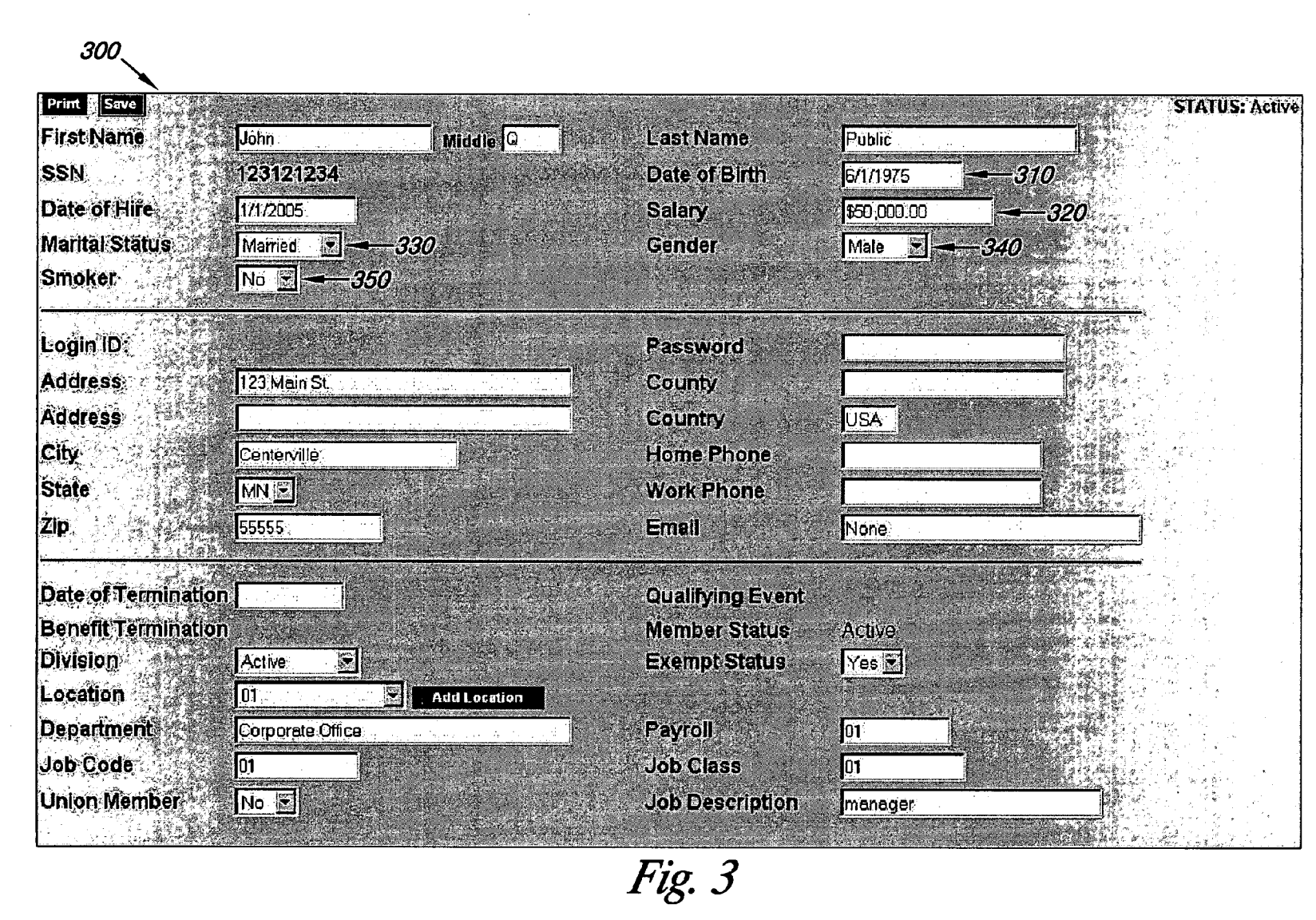

FIG. 3 is a viewable interface 300 illustrating an embodiment for receiving personal information according to the present disclosure. The viewable interface 300 includes various fields into which an individual can enter various personal information. These fields include a birth date field 310, a salary field 320, a marital status field 330, a gender field 340, and a smoking status field 350. In some embodiments, various additional fields can also be used for entering personal information.

In the example information shown in FIG. 3, the birth date field 310 includes a birth date entry of Jun. 1, 1975, the salary field 320 includes a salary entry of $50,000, the marital status field 330 includes a selection for Married, the gender field 340 includes a selection for Male, and the smoking status field 350 includes a selection for No.

Program instructions can execute to receive the personal information entered into the fields 310 through 350. Program instructions can execute to use such personal information to calculate estimated expenses to be incurred, e.g., 237 in FIG. 2, under a benefit plan by an individual and/or by others to be covered with the individual, as described in connection with the embodiments of FIGS. 2 and 6. For example, program instructions can execute to calculate a particular premium expense for an individual to participate in a benefit plan, based at least in part on the individual's age, marital status, gender, and/or smoking status. Program instructions can also execute to use such personal information to determine a recommended level of benefits for the individual and/or for others to be covered with the individual, as described in connection with the embodiments of FIGS. 5 and 7. As an example, program instructions can execute to recommend a particular life insurance benefit for an individual, based at least in part on the individual's age, salary, and marital status. In various embodiments of the present disclosure, the program instructions associated with the viewable interface 300 can be included in the program instructions 230 of the embodiment of FIG. 2.

FIG. 4 is a viewable interface 400 illustrating an embodiment for selecting benefit coverage according to the present disclosure. The viewable interface 400 includes various options for benefit coverage which an individual can select. These option include a waive benefit option 410, a single coverage option 420, a family coverage option 430, and dependent family member options 435. In some embodiments, various additional options can also be provided for selecting benefit coverage. In the example selections shown in FIG. 4, the family coverage option 430 is selected, along with the selected dependent family member options 435.

Program instructions can execute to receive selections for benefit coverage from the options 410 through 435. Program instructions can execute to use such benefit coverage selections to calculate estimated expenses to be incurred, e.g., 237 in FIG. 2, by an individual and/or by the individual's dependent family members to be covered with the individual, under a benefit plan. Program instructions can also execute to use such benefit coverage selections to determine a recommended level of benefits for the individual and/or for the individual's dependent family members to be covered with the individual, as described in more detail connection with the embodiments of FIGS. 5 and 7. In various embodiments of the present disclosure, the program instructions associated with the viewable interface 400 can be included in the program instructions 230 of the embodiment of FIG. 2.

FIG. 5 is a viewable interface 500 illustrating an embodiment for estimating benefits to be used according to the present disclosure. The viewable interface 500 includes various fields into which an individual can enter estimates of particular types and frequency of benefits to be used by the individual and/or by others to be covered with the individual under a benefit plan. These fields include medical services fields 510, first medical goods fields 523, second medical good fields 527, an outpatient surgery field 530, an inpatient surgery field 540, and a number of people field 550.

In the example estimates shown in FIG. 5, the medical services fields 510 include estimates of 1 medical primary care physician visit per year, 2 specialist visits per year, 2 routine wellness exams per year, 1 urgent care visit per year, and 2 emergency room visits per year. The first medical goods fields 523 include example estimates of 12 thirty-day generic prescription purchases per year, zero thirty-day brand prescription purchases per year, and zero thirty-day non-preferred prescription purchases per year. The second medical goods fields 527 include example estimates of zero ninety-day generic prescription purchases per year, zero ninety-day brand prescription purchases per year, and zero ninety-day non-preferred prescription purchases per year. Also in FIG. 5, the outpatient surgery field 530 includes an estimate of zero outpatient surgeries per year, the inpatient surgery field 540 includes an estimate of zero inpatient surgeries per year, and the number of people field 550 includes an estimate of zero people for inpatient visits per year.

Program instructions can execute to use some or all of the estimates in the fields 510 through 550 as the estimates of benefits to be used 217, as described in connection with the embodiment of FIG. 2. Program instructions can execute to use some or all of the estimates in the fields 510 through 550 to calculate estimated expenses to be incurred under a benefit plan by the individual and/or by others to be covered with the individual, as described in connection with the embodiments of FIGS. 2 and 6.

Program instructions can also execute to determine a recommended level of benefits for the individual and/or others to be covered with the individual under a benefit plan. Such recommended levels of benefits can be determined based on various sources, such as recommendations from sellers of benefit products, providers of benefit services, and/or statistically calculated recommended benefits, along with benefits available under terms of benefit plans. As an example, for medical benefits, medical professionals and/or health organizations can provide recommended medical benefits for various individuals. In various embodiments of the present disclosure, such recommended benefits can be stored in a database server, such as the database server 115 of FIG. 1. Program instructions can execute to store and/or access such recommended benefits.

For example, program instructions can execute to determine that a recommended level of benefits includes an annual routine wellness exam for each person over a particular age covered under a health benefit plan. In this example, program instructions can execute to use benefit coverage selections, such as the benefit coverage selections in the embodiment of FIG. 4, to determine persons to be covered with an individual under a health benefit plan. Also in this example, program instructions can execute to use personal information, such as the personal information in the embodiment of FIG. 3, to determine ages of the covered persons. Program instructions, for this example, can execute to communicate to an individual who is a potential participant in the health benefit plan, that a recommended level of benefits includes an annual routine wellness exam for particular persons to be covered under the health benefit plan. This communication can take various forms, such as a prompt displayed on the viewable interface 500, e.g., in the form of a "benefits buddy" icon/animated graphics character. In various embodiments of the present disclosure, program instructions can execute in response to receiving an estimate of benefits to be used, e.g., 217 in FIG. 2, that the estimate fails to meet a recommended level of benefits. However, in various embodiments, program instructions can execute to accept estimates, inputs, and/or selections for benefits and/or benefit plans that differ from such recommended levels. In various embodiments of the present disclosure, the program instructions associated with the viewable interface 500 can be included in the program instructions 230 of the embodiment of FIG. 2.

FIG. 6 is a viewable interface 600 illustrating an embodiment for displaying estimates of expenses to be incurred, e.g., 237 in FIG. 2, under various benefit plans, e.g., 231-1, . . . , 231-N in FIG. 2, according to the present disclosure. The viewable interface 600 includes a chart with various columns and rows. The columns include various medical benefit plans available to an individual, including a first medical benefit plan 601, a second medical benefit plan 602, a third medical benefit plan 603, and a fourth medical benefit plan 604, such as the available benefit plans described in connection with the embodiment of FIG. 2. The rows include expenses for particular medical benefits 610, such as the particular medical benefits described in connection with the embodiment of FIG. 5. The rows also include potential participant out-of-pocket expenses 620, health benefits account contributions 630, adjusted expenses 640, premium expenses 650, including premium expenses calculated per year and premium expenses calculated per pay period, and summary, e.g., total expenses 660. The viewable interface 600 also includes selection buttons 670.

In the example estimates shown in FIG. 6, the column for the first medical benefit plan 601 includes various expenses for the particular medical benefits 610, total out-of-pocket expenses 620 of $595, total health benefits account contributions 630 of zero dollars, total adjusted expenses 640 of $595, premium expenses 650 of zero dollars annually and zero dollars per pay period, total expenses 660 of $595, and a selection button 670, by which an individual can select to enroll as a participant in the first medical benefit plan 601.

The column for the second medical benefit plan 602 includes various expenses for the particular medical benefits 610, total out-of-pocket expenses 620 of $665, total health benefits account contributions 630 of zero dollars, total adjusted expenses 640 of $655, premium expenses 650 of $4,800 annually and $184.62 per pay period, total expenses 660 of $5,455, and a selection button 670, by which an individual can select to enroll as a participant in the second medical benefit plan 602.

The column for the third medical benefit plan 603 includes various expenses for the particular medical benefits 610, total out-of-pocket expenses 620 of $665, total health benefits account contributions 630 of zero dollars, total adjusted expenses 640 of $655, premium expenses 650 of $3,600 annually and $138.46 per pay period, total expenses 660 of $4,255, and a selection button 670, by which an individual can select to enroll as a participant in the third medical benefit plan 603.

The column for the fourth medical benefit plan 604 includes various expenses for the particular medical benefits 610, total out-of-pocket expenses 620 of $678, total health benefits account contributions 630 of $3,000, total adjusted expenses 640 of zero dollars, premium expenses 650 of $3,840 annually and $147.69 per pay period, total expenses 660 of $3,840, and a selection button 670, by which an individual can select to enroll as a participant in the fourth medical benefit plan 604.

Program instructions can execute to use some or all of the estimated values reflected in rows 610 through 660 in the comparison 239 of calculated estimates of expenses to be incurred 237, as described in connection with the embodiment of FIG. 2. That is, program instructions can execute to calculate the estimated expenses 610, 620, and 650 to be incurred by an individual and/or by others to be covered with the individual under each of the medical benefit plans 601 through 604, based on estimates of benefits to be used, e.g., 217 in FIG. 2, and estimates of expenses for benefits, 235 in FIG. 2, under the terms of the medical benefit plans, 231-1, . . . , 231-N in FIG. 2, as described in connection with the embodiments of FIGS. 2 and 5. Program instructions can also execute to calculate the health benefits account contributions 630 under each of the medical benefit plans 601 through 604, as described in connection with the embodiment of FIG. 2. Program instructions can further calculate under each of the medical benefit plans 601 through 604 the estimated expenses 640 and 660, which include the estimated expenses 620 and 650 as offset by funds from the health benefits account, received through the health benefits account contributions 630, also as described in connection with the embodiment of FIG. 2.

Program instructions can execute to display together in the viewable interface 600 a comparison of the estimated expenses for the medical benefit plans 601 through 604. In the embodiment of FIG. 6, estimated expenses for four medical benefit plans are displayed together, however in embodiments of the present disclosure, program instructions can execute to display together a comparison of estimated expenses for various numbers of benefit plans.

In some embodiments of the present disclosure, program instructions can execute to display medical benefit plans in a particular order based on the estimated expenses. In the viewable interface 600, the medical benefit plans 601 through 604 are displayed from left to right, based on the total out-of-pocket expenses 620, with a benefit plan having lower total out-of-pocket expenses 620 on the left and a benefit plan having higher total out-of-pocket expenses 620 on the right. In the embodiment of FIG. 6, the first medical benefit plan 601 has total out-of-pocket expenses 620 of $595, which is the lowest total out-of-pocket expenses 620 from among the medical benefit plans 601 through 604. Program instructions can execute to display benefit plans in a particular order based on the lowest total out-of-pocket expenses 620. Similarly, in various embodiments, program instructions can execute to display benefit plans in a particular order based on a lowest total adjusted expenses 640, a lowest premium expense 650, or a lowest total expenses 660. In various embodiments, such expenses can be independent from each other. For example, a benefit plan with lowest total out-of-pocket expenses 620 may or may not have highest premium expenses 650 and may or may not have lowest total expenses 660.

Program instructions can also execute to communicate to an individual who is a potential participant in the health benefit plan, that a particular benefit plan has a lowest expense. This communication can take various forms, such as a prompt in the form of a "benefits buddy" shown as an icon and/or animated graphics character and displayed on the viewable interface 600. In various embodiments of the present disclosure, the program instructions associated with the viewable interface 600 can be included in the program instructions 230 of the embodiment of FIG. 2.

FIG. 7 is a viewable interface 700 illustrating an embodiment for displaying a recommended level of benefits according to the present disclosure. The viewable interface 700 includes a recommendation table 710, potential participant life insurance calculations 720, and spouse life insurance calculations 730. The potential participant life insurance calculations 720 include a selectable multiplying factor 721, an income field 722, a basic life insurance field 723, a supplemental life insurance field 724, a marketplace life insurance field 725, an other life insurance field 726, a recommended level of benefits 727, a current level of benefits 728, and a difference of benefits 729.

The recommendation table 710 includes life insurance benefits generally recommended in the life insurance industry. In various embodiments of the present disclosure, program instruction can execute to store and/or access such recommended benefits, for example, by storing them in a database server, such as the database server 115 of FIG. 1.

In the examples shown in FIG. 7, the selectable multiplying factor 721 is a selected factor of 10 times, the income field 722 includes an entry of $36,000, the basic life insurance field 723 includes an entry of $50,000, the supplemental life insurance field 724 includes an entry of $50,000, the marketplace life insurance field 725 includes an entry of zero dollars, and the other life insurance field 726 includes an entry of $100,000.

Program instructions can execute to use the inputs of 721 through 726 from a potential participant in a life insurance benefit plan to perform the potential participant life insurance calculations 720. Program instructions can execute to multiply the entry of $36,000 in the income field 722 by the selected factor of 10 times from the selectable multiplying factor 721, to obtain the calculated recommended level of benefits 727 of $360,000 in life insurance. Program instructions can execute to add the $50,000 entry in the basic life insurance field 723, the $50,000 entry in the supplemental life insurance field 724, the zero dollars entry in the marketplace life insurance field 725, and the $100,000 entry in the other life insurance field 726 to obtain the calculated current level of benefits 728 of $200,000 in current life insurance. Program instructions can also execute to subtract the $200,000 current level of benefits 728 from the $360,000 recommended level of benefits 727 to obtain the calculated difference of benefits 729 of $160,000 in life insurance. Similarly, program instructions can also execute to perform the spouse life insurance calculations 730. In various embodiments of the present disclosure, the program instructions associated with the viewable interface 700 can be included in the program instructions 230 of the embodiment of FIG. 2.

Although specific embodiments have been illustrated and described herein, those of ordinary skill in the art will appreciate that an arrangement calculated to achieve the same techniques can be substituted for the specific embodiments shown. This disclosure is intended to cover all adaptations or variations of various embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that embodiments of the present disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A tangible computer readable medium including instructions for causing a device to perform a method, the method comprising:
   providing terms for a number of benefit plans available to a potential participant;
   receiving an estimate of benefits to be used by the potential participant; displaying together an estimate of expenses to be incurred by the potential participant under each of the benefit plans based on the terms and the estimate of benefits to be used;
   determining a recommended level of benefits for the potential participant from the number of benefit plans, based on the estimate of benefits to be used by the potential participant;
   receiving, while displaying the estimate of expenses, a selection for enrolling the potential participant into a particular benefit plan from among the number of benefit plans; and communicating that the benefit selection fails to meet the recommended level, in response to receiving from the potential participant a benefit selection that fails to meet the recommended level of benefits for the potential participant.

2. The medium of claim 1, wherein the method includes: receiving estimates for particular types of benefits to be used by the potential participant; and displaying an estimate of expenses to be incurred by the potential participant for each of the particular types of benefits under each of the benefit plans based on the estimates for the particular types of benefits to be used.

3. The medium of claim 1, wherein the method includes receiving an estimate of benefits to be used by the potential participant, based on a forecast of future needs for the potential participant.

4. The medium of claim 1, wherein the method includes receiving an estimate of benefits to be used by the potential participant for a particular period of time.

5. The medium of claim 1, wherein the method includes: receiving an estimate of contributions to be made to a benefits account for the potential participant; and displaying an estimate of expenses to be incurred by the potential participant and to be offset by funds from the benefits account under each of the benefit plans based on the estimate of contributions.

6. The medium of claim 1, wherein the method includes displaying an estimate of total premium expenses to be incurred by the potential participant under each of the benefit plans based on the terms.

7. The medium of claim 1, wherein the method includes displaying an estimate of total out-of-pocket expenses to be incurred by the potential participant under each of the benefit plans based on the estimate of benefits to be used.

8. A tangible computer readable medium including instructions for causing a device to perform a method, the method comprising: determining a number of health care plans available to an individual;
   receiving an estimate for health products and health services to be used by the individual; and calculating estimates of expenses for the health products and the health services under each of the health care plans;
   determining a recommended level of benefits for the individual from the number of health care plans, based on the estimate for health products and health services to be used by the individual;
   receiving, while displaying the estimate of expenses, a selection for enrolling the individual into a particular benefit plan from among the number of health care plans; and communicating that the benefit selection fails to meet the recommended level, in response to receiving from the individual a benefit selection that fails to meet the recommended level of benefits for the individual.

9. The medium of claim 8, wherein the method includes determining the number of health care plans based on a selection from an employer of the individual.

10. The medium of claim 8, wherein the method includes calculating the estimates of expenses based on a copay, a deductible, and a coinsurance percentage for each of the health cam plans.

11. The medium of claim 8, wherein the method includes calculating the estimates of premium expenses for each pay period for an employer of the individual.

12. The medium of claim 8, wherein the method includes calculating the estimates of expenses including an offset of an estimate of contributions to be made by an employer of the individual.

13. The medium of claim 8, wherein the method includes calculating the estimates of expenses including an offset of funds from a health benefits account selected from the group, including: a health savings account; a flexible savings account; and a health reimbursement account.

14. The medium of claim 8, wherein the method includes:
displaying an estimate of expenses for a particular health care plan with a lowest total of out-of pocket expenses from among the number of health care plans; and
displaying with the estimate of expenses for the particular health care plan a message indicating that the particular health care plan has the lowest total of out-of-pocket expenses from among the number of health care plans.

15. The medium of claim 8, wherein the method includes displaying together the estimates of expenses.

16. The medium of claim 15, wherein the method includes displaying with the estimates of expenses a message indicating which particular health care plan has a lowest total out-of-pocket expenses from among the number of health care plans.

17. A tangible computer readable medium including instructions for causing a device to perform a method, the method comprising:
receiving particular log-in information for an individual;
determining available benefit plans for the individual, based on the particular log-in information; receiving personal information for the individual; determining a recommended level of benefits for the individual from the available benefit plans, based on the personal information; receiving, while displaying the estimate of expenses, a selection for enrolling the individual into a particular benefit plan from among the number of benefit plans; and communicating that the benefit selection fails to meet the recommended level, in response to receiving from the individual a benefit selection that fails to meet the recommended level of benefits for the individual.

18. The medium of claim 17, wherein the method includes communicating to the individual the recommended level of benefits for the individual from the available benefit plans.

19. The medium of claim 17, wherein the method includes:
receiving a benefit selection for the individual from the available benefit plans; and determining whether the benefit selection meets the recommended level of benefits for the individual.

20. A system comprising: a processor; a memory, connected to the processor; and program instructions storable in the memory and executable by the processor to: receive particular log-in information;
determine a particular individual and particular available health benefit plans associated with the particular log-in information; receive an estimate of benefits to be used by the particular individual; display estimates of health care expenses for the particular individual under each of the particular available health benefit plans;
determine a recommended level of benefits for the particular individual from the available health benefit plans, based on the estimate of benefits to be used by the particular individual;
receive, while displaying the estimate of expenses, a selection for enrolling the individual in a particular health benefit plan from among the number of health benefit plans; and communicate that the benefit selection fails to meet the recommended level, in response to receiving from the particular individual a benefit selection that fails to meet the recommended level of benefits for the particular individual.

21. The system of claim 20 including program instructions executable to display together the estimates of health care expenses based on an estimate of health care to be used by the particular individual.

22. The system of claim 20 including program instructions executable to display a message indicating which of the particular available health benefit plans offers a lowest estimated total of out-of-pocket health care expenses for the particular individual based on an estimate of health care to be used by the particular individual.

* * * * *